United States Patent [19]

Moechnig

[11] Patent Number: 5,242,690
[45] Date of Patent: Sep. 7, 1993

[54] INERT GRANULAR CARRIER FOR CHEMICALS

[75] Inventor: Bruce W. Moechnig, Cologne, Minn.

[73] Assignee: Cargill, Incorporated, Minneapolis, Minn.

[21] Appl. No.: 837,681

[22] Filed: Feb. 18, 1992

Related U.S. Application Data

[63] Continuation of Ser. No. 603,129, Oct. 25, 1990, abandoned.

[51] Int. Cl.$^5$ .................. A01N 25/00; A01N 25/08
[52] U.S. Cl. ................... 424/405; 424/409; 424/410; 424/DIG. 8; 424/489; 514/772; 71/1
[58] Field of Search ............ 424/404, 403, 410, 405, 424/489, DIG. 8, 408, 409; 71/92, 1; 514/122, 772, 617

[56] References Cited

U.S. PATENT DOCUMENTS

| | | | |
|---|---|---|---|
| 3,117,057 | 1/1964 | Snyder | 514/122 |
| 3,737,551 | 6/1973 | Karsten et al. | 514/772 |
| 4,160,824 | 7/1979 | Inazuka et al. | 514/122 |
| 4,511,581 | 4/1985 | Ohsumi et al. | 514/617 |
| 4,563,344 | 1/1986 | Kotz et al. | 424/410 |
| 4,936,901 | 6/1990 | Surgant, Sr. et al. | 71/92 |

OTHER PUBLICATIONS

H. W. Ross, "Available Granular Carriers-Properties and General Processing Methods," *Pesticide Formulations and Applications Systems: Second Conference, ASTM STP795*, K. G. Seymour, Ed., American Society for Testing and Materials, 32–44 (1983).

*Primary Examiner*—Thurman K. Page
*Assistant Examiner*—G. S. Kishore
*Attorney, Agent, or Firm*—Fitch, Even, Tabin & Flannery

[57] ABSTRACT

A granular substrate, and method for preparation thereof, is provided for use with herbicide, fungicide, and/or insecticide formulations, the substrate comprising an agglomerated grain dust and/or hulls in combination with a binder, particularly a lignosulfonate binder. The granular substrate can readily disintegrate when wetted or maintain its integrity under wetting conditions.

11 Claims, No Drawings ial INERT GRANULAR CARRIER FOR CHEMICALS

This application is a continuation of application Ser. No. 07/603,129 filed Oct. 25, 1990, abandoned.

The present invention relates generally to an inert, granular substrate for carrying pesticide, herbicide, fungicide and/or fertilizer formulations, and, more particularly, it relates to an organic, biodegradable granular substrate which maintains its integrity when dry, but which can readily disperse on the ground when subjected to wetting conditions.

BACKGROUND OF THE INVENTION

Granular inert carriers have been heretofore used to carry pesticide, herbicide, fungicide and fertilizer formulations. These carriers have been broadly categorized as inorganic and botanical by Ross, H. W., "Available Granual or Carriers—Properties and General Processing Methods", Pesticide Formulations and Application Systems: Second Conference, ASTM STP 795, K.G. Seymour, Ed., American Society for Testing Materials, 1983, pp. 32–44. The inorganic category comprises clays, sand and vermiculite. While low in cost, the clays oftentimes need to be treated with a deactivator prior to formulation to prevent decomposition of the active ingredient.

The botanical category comprises corn cobs, walnut shells, rice hulls, and wood. Corn cobs have been a primary source of inert granular carriers, but continued expansion of the use of combine harvesters and occasional drought conditions have raised questions as to the adequacy of supply of corn cobs and have driven up its cost.

The botanical carriers, along with the low-volatile matter clays, sand, and vermiculite all break down slowly, or not at all, when applied to the soil. As a result, intact granules containing active ingredients of pesticide, herbicide, and fertilized fungicide may remain available for long periods of time on the soil surface. This has resulted in reports of bird kills and subsequent action by the Environmental Protection Agency (EPA) to ban, or severely restrict, the use of some products to mitigate this problem. Thus, an inert carrier which could maintain its integrity during formulation but disintegrate when wetted by rainfall or irrigation conditions after application would be advantageous in reducing the likelihood of birds ingesting unwanted materials.

However, in some circumstances it may be desirable to maintain the integrity of the substrate on the ground, even when subjected to wetting conditions. Accordingly, there has been a demand for an improved granular carrier which can have controlled disintegration for utilization under varying ground or soil conditions while offering protection against avian toxicity when desired.

A principle object of this invention is, therefore, to provide an improved inert granular substrate for carrying pesticide, herbicide, fungicide and/or fertilizer formulations.

A more particular object of the invention is the provision of an inert, granular substrate for carrying pesticide, herbicide, fungicide and fertilizer formulations, the disintegration of which is controllable.

A still more particular object of the invention is the provision of an organic, biodegradable granular substrate which maintains its integrity when dry, but readily disperses on the ground when subjected to wetting conditions.

A further object of the invention is the provision of an inert granular substrate, which is organic and biodegradable but which can readily disperse on the ground when subjected to wetting as by rainfall or irrigation.

Another object of the invention is the provision of an inert, granular substrate which is more economical than corn cobs, and which can be prepared from grain dust and grain hulls.

Still another object of this invention is the provision of an improved method for making an inert, granular substrate for carrying pesticide, herbicide, fungicide and fertilizer formations.

Still another and additional object of the invention is the provision of an improved method for making an inert, granular substrate under controlled conditions which permits adjustment of the rate of disintegration of the substrate on the ground under wetting conditions.

Further objects and advantages of the invention will become apparent by reference to the following description.

SUMMARY OF THE INVENTION

The inert, granular substrate for carrying pesticide, herbicide, fungicide and/or fertilizer formulations of this invention has the following properties:

| Packed Bulk density | 0.48–0.56 grams per cubic centimeter |
|---|---|
| Absorptive capacity | 25%–50% |
| pH, 5% slurry | 5–8 |
| Resistance to attrition | greater than 95% |
| Moisture content | 3%–15% |
| Particle size | 10–40 mesh nominal |
| Water disintegratability | Greater than 2 minutes |

Bulk density is measured by the free-fall bulk density test described in ASTM Standard Test Method E727-80. Packed bulk density is measured by placing a graduated cylinder containing the carrier on a vibrating table for 60 minutes, and then reading the volume occupied.

The absorptive capacity of the granular substrate is determined by weighing out 100 grams of the granules and placing them in a pan. A small amount of water is misted onto the surface of the granules followed by general agitation to mix the water and granular substrate. This procedure is repeated until the granules begin to stick together forming larger agglomerates. At this point, a sample is taken and the moisture content determined using an air-oven procedure. The moisture content, expressed as the weight of water removed in the drying process divided by the dry weight of the granules, is taken to be the water absorptivity.

The pH of the granular substrate is determined using a pH meter on a slurry comprising 5 grams of substrate and 95 milliliters of deionized water. Acid or base can be added during processing to adjust the pH to a desired level.

The resistance to attrition is measured by the ASTM Standard Test Method E728-80, using 13 millimeter steel balls. It is noted that the 13 millimeter steel balls are somewhat smaller than those specified in the test method.

The water disintegratability is measured by placing the granular substrate in a beaker of water with stirring and determining the time of disintegration. In accord with the methods of the invention, the water disintegratability can be varied by adjusting the procedure for making the granular substrate.

Moisture content is measured by drying in an oven overnight at 65° C. (150° F.).

The granular substrate of the invention preferably comprises a grain dust which may include grain hulls and a binder. The loose grain dust should be dry with no signs of heating or clumping, and have a bulk density, loose, in excess of 20 pounds per cubic foot (0.32 grams per cubic centimeter), and 80% should pass through a 35 mesh sieve and 50% through a 100 mesh sieve. Preferably, the grain dust should have a bulk density of between about 20 and 25 pounds per cubic foot (0.32 grams per cubic centimeter to 0.40 grams per cubic centimeter) and 50% should pass through a 100 mesh sieve. It has been found that the grain dust is best derived from operations which handle mixed grains rather than small grains exclusively. Hulls may be included in the grain dust or may be added back to grain dust provided they are ground to pass a 35 mesh sieve.

A bulk density below 20 pounds per cubic foot does not give desired results and, more particularly, lower bulk densities require excessive amounts of binder. The hulls do not significantly change the properties of the grain dust when they pass a 35 mesh sieve after grinding.

The grain dust will have a fiber content of less than about 15% and an ash of less than about 10%. The nitrogen free extract (NFE) should exceed about 60%.

The grain dust, with or without hulls, is mixed with a binder and the mixture is then agglomerated to provide the granular substrate of the invention.

The binder is a liquid lignosulfonate product provided as a by-product of the manufacture of paper, and is preferably provided as sodium or calcium lignosulfonate. The binder has a dry solids context of between about 35% and 55% and is added to the dust at a level of between about 0.80 pounds of binder to about 1.80 pounds of binder (wet bases) per pound of dust. Preferably, the binder will have a dry solids context of between about 40% to about 50% and will be added at a level between about 0.90 pounds to about 1.20 pounds (wet bases) per pound of dust. The substrate comprises between about 30% and about 40% lignosulfonate on a dry basis.

The manner of agglomeration is important to achieve the granular substrate of the invention. There are three currently used methods for agglomerating fine powders, referred to as agitation agglomeration, disc pelletizing agglomeration, and compaction agglomeration. The agitation and disc pelletizing methods produce granular products, whereas the compaction agglomeration produces pellets which break into a powder without granular structure. Accordingly, the compaction agglomeration method is not desirable in making the substrate of the invention.

In accord with the agitation method, the dust is wetted with the lignosulfonate binder while being mechanically agitated to provide the granules. A disc pelletizer is employed to provide the granules in the pelletizing method. While either method can be employed, one may be preferred over another depending upon the size distribution in the grain dust.

The granular substrate is heated in a drier to a temperature between 250° F. and 400° F. for a period of from 0.50 hours to 0.25 hours so as to achieve a moisture between 3% and 15%. At the higher temperatures, the granules become more resistant to disintegration and at a temperature of 400.F. for 0.25 hours, the granules were substantially insoluble in water. On the other hand, drying at 250° F. for 0.50 hours resulted in a granular substrate which disintegrated in water in 2 minutes. Intermediate temperatures and times provided particles which disintegrated at intermediate times. Times and temperatures can be selected so as to achieve the moisture levels specified, but the temperature should be sufficiently high to provide the attrition property to the granular substrate. When the substrate does not disintegrate in water in 16 hours, it is considered substantially insoluble.

After agglomeration and drying, the granular substrate is screened to provide the desired particle size, preferably to remove granules having a sieve size of less than 40 mesh and greater than 10 mesh.

The granular substrate is impregnated with herbicide, pesticide, fungicide and/or fertilizer by usual techniques at desired levels.

High levels of lignosulfonate has been found to deter birds from eating the granules so to reduce avian toxicity. In addition, tannic acid may be added to the substrate to deter birds from eating the granules.

The granular substrate of the invention does not require pre-conditioning prior to application of active ingredients. Also, the granular substrate provides for utilization of grain dust which, historically, has been difficult to handle and market. In addition, the grain dust is an economical ingredient which permits the manufacture of a low cost product.

Binders having equivalent properties to the lignosulfonate may be used, but economics generally prevent their use. Sources of binder may be saccharides and polysaccharides including glucose, sucrose, molasses and starch.

The invention is more particularly described in the following Examples.

EXAMPLE 1

Grain dust was obtained from the below indicated locations and substrate samples were prepared by weighing out 150 grams of dust which was screened through a 35 mesh sieve. The hulls were first separated and ground to pass a 35 mesh sieve and added back to the grain dust. The liquid binder was added at the indicated levels, the binder comprising calcium lignosulfonate at 40% dry solids (d.s.). Agglomeration was effected in a food processor to simulate the effect of agitation agglomeration, as, for example, in a Bepex Turbulizer. The binder was added in the food processor until the dust formed agglomerates. A visual determination of the end point was used, and at such point the amount of liquid lignosulfonate added was determined. The agglomerated material was oven dried to a moisture level of less than 3% at a temperature of 120° F. for 16 hours, and the substrate was screened to remove particles larger than 10 mesh and smaller than 40 mesh. Analysis gave the following results.

| Location | Bulk Density lbs./ft.$^3$ | | pH | Absorptivity % | Attrition | Lignosulfonate /dust |
|---|---|---|---|---|---|---|
| | Loose | Packed | | | | |
| Savage, MN | 34.7 | 37.3 | 4.4 | 47.5 | >95 | 1.11 |
| Topeka, KS | 32.6 | 34.3 | 4.5 | 29.9 | >95 | 0.94 |
| Maumee, OH | 30.9 | 33.0 | 4.4 | 39.7 | >95 | 1.13 |
| Portland, OR | 21.4 | 22.6 | 4.5 | 49.3 | >95 | 1.70 |
| Houston, TX | 24.2 | 25.6 | 4.5 | 49.3 | >95 | 1.58 |
| Chesapeake, | 29.8 | 32.3 | 4.7 | 41.6 | >95 | 0.88 |

-continued

| Location | Bulk Density lbs./ft.$^3$ | | pH | Absorptivity % | Attrition | Lignosulfonate /dust |
|---|---|---|---|---|---|---|
| | Loose | Packed | | | | |
| VA | | | | | | |

The lignosulfonate/dust ratio is expressed in parts of binder per one part of dust on weight to weight (w/w) basis.

Bulk densities of the dusts exhibited a wide range of values. They can, however, be separated into two groups. The granular substrates made from the Savage, Topeka, Maumee, and Chesapeake samples had bulk densities that were all well within an acceptable range and higher than the density of comparable corncob products. The pH and water absorptivity of these samples were also in acceptable ranges.

The samples from Portland and Houston produced granules with unacceptably low bulk densities. These samples also took significantly more lignosulfonate to agglomerate than the others.

The samples all disintegrated in less than 2 minutes when placed in water and stirred.

EXAMPLE 2

In this Example, samples of dust containing the highest and lowest percentage of hulls were screened, agglomerating only the portion that passed through the 35-mesh sieve. A visual end point was again determined as in Example 1, and the amount of lignosulfonate used measured. A comparison of the properties of the granular substrates samples made from each dust, with and without the hulls, is presented below.

| Location | Hulls Added | Bulk Density lbs./ft.$^3$ | | pH | Attrition | Absorptivity |
|---|---|---|---|---|---|---|
| | | Loose | Packed | | | |
| Savage, MN | Yes | 34.7 | 37.3 | 4.4 | >95 | 47.5 |
| | No | 34.6 | 36.4 | 4.6 | >95 | 39.9 |
| Chesapeake, VA | Yes | 29.8 | 32.3 | 4.7 | >95 | 41.6 |
| | No | 34.4 | 38.1 | 4.6 | >95 | 32.1 |

EXAMPLE 3

To determine the reason for the poor performance of the Portland and Houston samples, the bulk densities of the dust samples as received were measured. These results are presented below.

| Location | Bulk Density, lbs./ft.$^3$ |
|---|---|
| Savage, MN | 22.7 |
| Portland, OR | 15.2 |
| Houston, TX | 16.3 |
| Chesapeake, VA | 20.8 |

A difference of more than 4 lbs./ft.$^3$ was found between the dusts that produced acceptable substrates and those that did not. This suggests that the bulk density of the raw dust can be used as a means of determining whether or not a given lot of dust will produce acceptable granules.

The samples of dust from Portland and Houston, with the hulls ground and added back, were screened and the various size fractions examined under a microscope. Comparison of these samples with comparable fractions from the Savage and Chesapeake samples revealed the presence of significantly more hull and "hair-like" particles in the −60 to +120 mesh portions of the Portland and Houston samples. These flat and elongated particles apparently interfered with the close packing of the particles needed to achieve acceptable bulk densities.

The type of grain being handled affects the amount of hull and "hair-like" particles present in the dust. Visual inspection of the Portland and Houston samples indicates they were collected while handling small grains almost exclusively. The remaining samples, while containing some dust from small grains, also included dust from corn, soybeans, or milo. Thus, dust from the handling of small grains is to be avoided.

EXAMPLE 4

This Example illustrates the effect of using the agitation method and the disc pelletizer method for agglomeration. Samples were prepared as in Example 1, with the following results.

| Location | Method | Lignosulfonate/Dust | Bulk Density of Substrate lbs./ft.$^3$ | |
|---|---|---|---|---|
| | | | Loose | Packed |
| Savage, MN | Agitation | 1.11 | 34.7 | 37.3 |
| | Disc | 1.13 | 27.5 | 29.8 |
| Chesapeake, VA | Agitation | 0.88 | 29.8 | 32.3 |
| | Disc | 1.20 | 30.4 | 33.6 |
| | Disc | 1.20 | 29.9 | 33.7 |
| | Disc | 1.14 | 28.4 | 31.6 |
| | Disc | 1.08 | 26.2 | 29.0 |
| Portland, OR | Agitation | 1.70 | 21.4 | 22.6 |
| | Agitation | 1.75 | 22.3 | 23.9 |
| | Agitation | 1.69 | 20.3 | 22.4 |
| | Agitation | 1.60 | 20.5 | 22.9 |
| | Disc | 1.94 | 24.8 | 26.3 |
| Houston, TX | Agitation | 1.58 | 24.2 | 25.6 |
| | Agitation | 1.60 | 25.6 | 27.9 |
| | Agitation | 1.52 | 25.6 | 28.4 |
| | Agitation | 1.44 | 22.7 | 25.6 |
| | Disc. | 1.84 | 25.0 | 26.5 |
| Maumee, OH | Agitation | 1.13 | 30.9 | 33.0 |
| | Agitation | 1.13 | 31.7 | 33.8 |
| | Agitation | 1.13 | 30.7 | 33.4 |
| | Agitation | 1.13 | 30.9 | 34.0 |
| | Agitation | 1.13 | 38.3 | 31.5 |
| | Disc | 1.13 | 25.5 | 27.2 |
| | Disc | 1.13 | 20.3 | 22.3 |
| | Disc | 1.13 | 22.3 | 23.2 |
| | Disc | 1.13 | 20.6 | 22.4 |

Comparison of the agitation method of agglomeration with the disc pelletizing method shows mixed results. On the Savage and Maumee samples, the disc pelletizer produced a lighter product than when the food processor was used. The remaining samples (Chesapeake, Portland and Houston) showed little difference in bulk density as a result of the agglomeration method used. While the reason for the difference is not clear, the Savage and Maumee samples contain higher percentages of material in the −140 to +200 mesh range. These particles may respond more to agitation than to relatively mild mixing that occurs in the disc pelletizer. However, satisfactory substrates were provided by each method.

To illustrate the effect of compaction granulation, samples of the dust from Topeka and Chesapeake were compacted into cylindrical pellets using a Carver Laboratory Press. Lignosulfonate levels of 3,7, and 14% (40% d.s.) and compaction pressures of 5, 10, 30 and 30 kpsi were used. Selected pellets were dried and crushed to determine if this method would yield an acceptable granule. After drying, the pellets broke into a powder when crushed, retaining no granular structure. Thus, compaction granulation is not an effective means for granulation.

EXAMPLE 5

The lignosulfonate binder used in the prior Examples is a by-product of the paper industry and is marketed as a 60% d.s. solution. In the prior Examples this binder was diluted down to 40% d.s. In this Example, the amount and concentration of the binder was varied to determine how these two factors affect the properties of the granules produced.

Samples of dust from Chesapeake, Portland and Houston were agglomerated with various levels of lignosulfonate at 40% d.s. The resultant physical properties of the substrate is shown in the first three sets of data below. In addition, samples of dust from Chespeake were agglomerated with various levels of lignosulfonate at 20% d.s. These results are presented in the final set of data below.

| Location | Ratio, Lignosulfonate /dust | Bulk Density lbs./ft.$^3$ | | Resistance to Attrition % | Geometric Mean, Diameter, $\mu$m |
|---|---|---|---|---|---|
| | | Loose | Packer | | |
| Chesapeake, VA | 1.20 | 29.9 | 33.7 | 98.0 | 1200 |
| Chesapeake, VA | 1.14 | 28.4 | 31.6 | | 1165 |
| Chesapeake, VA | 1.08 | 26.2 | 29.0 | 95.0 | 1020 |
| Portland, OR | 1.75 | 22.3 | 23.9 | 99.0 | 1245 |
| Portland, OR | 1.69 | 20.3 | 22.4 | | 1105 |
| Portland, OR | 1.60 | 20.5 | 22.9 | 97.2 | 975 |
| Houston, TX | 1.60 | 25.6 | 27.9 | | 1120 |
| Houston, TX | 1.52 | 25.6 | 28.4 | | 935 |
| Houston, TX | 1.44 | 22.7 | 25.6 | | 820 |
| Chesapeake, VA | 1.07 | 31.1 | 33.4 | | 1345 |
| Chesapeake, VA | 0.95 | 26.0 | 28.8 | | 905 |
| Chesapeake, VA | 0.93 | 23.6 | 26.3 | | 810 |
| Chesapeake, VA | 0.83 | 22.6 | 24.7 | | 740 |

The bulk density of the granules was directly affected by the amount of lignosulfonate added. Higher levels of lignosulfonate result in a heavier product. It also appears that below a certain lignosulfonate/dust ratio, the loss in bulk density becomes very pronounced.

Resistance to attrition, which is a measure of how easily the product will break up in handling, decreased as the amount of lignosulfonate was reduced. The lowest value seen in the samples tested was 95.0%, which is slightly below that for corncobs, but well above the values quoted for clay products.

The geometric mean diameter is a weighted average particle size for a sample containing particles with a range of sizes. It is determined by screening the sample through a series of sieves, weighing the fraction retained on each sieve, and then calculating the mean diameter based on the sieve sizes and weights.

For these samples, the geometric mean diameter showed the same relationship as resistance to attrition. Reducing the amount of lignosulfonate shifted the particle size distribution from larger to smaller particles, resulting in lower geometric mean diameters.

EXAMPLE 6

Samples of grain dust from Maumee were agglomerated in a food processor with various concentrations of lignosulfonate using a constant ratio of lignosulfonate solution to dust. The physical properties of the resultant granules are presented below.

| Location | % d.s. | Bulk Density lbs./ft.$^3$ | | Attrition % | Diameter, $\mu$m |
|---|---|---|---|---|---|
| | | Loose | Packed | | |
| Maumee | 50 | 34.5 | 36.9 | 99.6 | 1405 |
| Maumee | 40 | 31.7 | 33.8 | | 1220 |
| Maumee | 40 | 30.9 | 33.0 | | 1120 |
| Maumee | 30 | 28.8 | 31.0 | 99.0 | 1130 |

Reducing the concentration of lignosulfonate, while maintaining a constant ratio of lignosulfonate/dust, had the same effect as reducing the amount of lignosulfonate solution used. Bulk density and geometric mean diameter of the granules both decreased with a decrease in the lignosulfonate concentration. It is to be noted that at 30% d.s., the granules still exhibited bulk densities that were as good as, or better, than corncobs.

EXAMPLE 7

A sample prepared in accord with Example 1 was placed in an oven that had been preheated to 400° F. and allowed to remain in the oven until the oven temperature had recovered to its original level. The substrate had a moisture level of less than 3%. The substrate was insoluble when put in a beaker of water and allowed to stand for 16 hours. The product emulated use of corn cobs as a substrate.

A new and unique substrate has been provided which fills an existing need for effectively utilizing herbicide, pesticide, fungicide and fertilizer on the ground. The method of making the substrate permits variation of disintegration rates to provide desired effectiveness of the active ingredients.

The various features of the invention believed to be new are set forth in the following claims.

What is claimed is:

1. A biodegradable granular substrate comprising a grain dust having a bulk density at least about 20 pounds per cubic foot, no more than about 10% ash and a fiber content of no more than about 15%, where 80% of said grain dust passes through a 35 mesh sieve and 50% passes through a 100 mesh sieve, and a binder in an amount of from about 0.80 pounds to about 1.80 pounds of binder wet basis per pound of dust to thereby form a biodegradable substrate where said binder is selected from the group consisting of lignosulfonate, glucose, sucrose, molasses and starch, and said biodegradable substrate is adapted for impregnation with herbicide, pesticide, fungicide, fertilizers or mixtures thereof, wherein said substrate includes the dust agglomerated with the binder and wherein the substrate has a packed bulk density between about 0.48 and about 0.56 grams per cubic centimeter, an absorptive capacity of between about 25% and 50%, a resistance to attraction greater than 95%, a moisture content between about 3% and 13%, a particle size of 10 to 40 mesh and a water disintegratability of at least 2 minutes.

2. A granular substrate in accord with claim 1 wherein the binder is a lignosulfonate.

3. A granular substrate in accord with claim 1 wherein the binder is calcium lignosulfonate.

4. A granular substrate in accord with claim 1 wherein the grain dust has a bulk density, loose, between about 20 pounds per cubic foot and about 25 pounds per cubic foot.

5. A method for making a biodegradable granular substrate used as a carrier for herbicide, fungicide, pesticide, fertilizers or mixtures thereof comprising the steps of mixing a grain dust with a liquid binder at a level between about 0.80 pounds to about 1.8 pounds of binder per pound of grain dust to form a mixture, the grain dust having no more than about 15% ash, a bulk density, loose, at least of about 20 pounds per cubic foot, and a filler content of less than about 15%, where 80% of the grain dust passes through a 35 mesh sieve and 50% passes through a 100 mesh sieve, the liquid binder having a dry solids content between about 35% and 55%, agglomerating the mixture to form an agglomerated mixture, and drying the agglomerated mixture to a moisture content between about 3% and about 15%, where said substrate comprises a binder selected from the group consisting of lignosulfonate, glucose, sucrose, molasses and starch.

6. A method in accord with claim 5 wherein the binder is a lignosulfonate.

7. A method in accord with claim 5 wherein agglomeration is effected by agitation or disc pellitizing.

8. A method in accord with claim 5 wherein the grain dust, loose, has a bulk density between about 20 pounds per cubic foot and about 25 pounds per cubic foot.

9. The composition of claim 1, wherein the binder is used in an amount of between about 0.90 pounds to about 1.20 pounds on a wet bases per pound of dust.

10. The composition of claim 5 wherein the binder is used in an amount of between about 0.90 pounds to about 1.20 pounds on a wet bases per pound of dust.

11. A granulate substrate in accord with claim 3 wherein the grain dust has a bulk density, loose, between about 20 pounds per cubic foot and about 25 pounds per cubic foot.

* * * * *